United States Patent [19]

Mogolesko et al.

[11] 4,140,714

[45] Feb. 20, 1979

[54] PROCESS FOR PREPARING N-(1,1-DIMETHYL-3-OXOBUTYL)ACRYLAMIDE FROM A 2-VINYL-1,3(4H)OXAZINE SULFATE

[75] Inventors: Paul D. Mogolesko; Karel F. Bernady, both of Belle Mead, N.J.

[73] Assignee: American Cyanamid Company, Stamford, Conn.

[21] Appl. No.: 920,101

[22] Filed: Jun. 28, 1978

[51] Int. Cl.$^2$ .................... C07C 29/00; C07C 102/00
[52] U.S. Cl. ................................. 260/561 N; 544/88
[58] Field of Search ............... 260/561 N; 544/88, 97

[56] References Cited

U.S. PATENT DOCUMENTS

| | | | |
|---|---|---|---|
| 3,531,525 | 9/1970 | Hope et al. | 260/561 N |
| 3,542,867 | 11/1970 | Foecking | 260/561 N |
| 3,542,875 | 11/1970 | Raymond | 260/561 N |
| 3,575,890 | 4/1971 | Litt et al. | 544/88 |
| 3,649,688 | 3/1972 | Gordon et al. | 260/561 N |

FOREIGN PATENT DOCUMENTS 233130 2/1961 Australia .................... 544/88

Primary Examiner—Allen B. Curtis
Attorney, Agent, or Firm—Charles F. Costello, Jr.

[57] ABSTRACT

A process is disclosed whereby 5,6-dihydro-6-hydroxy-4,4,6-trimethyl-2-vinyl-1,3(4H)-oxazine sulfate (1:1) is neutralized or alkalized under carefully controlled conditions to produce N-(1,1-dimethyl-3-oxobutyl)acrylamide, a reactive monomer useful for preparing polymeric components of photographic films and adhesives.

12 Claims, No Drawings

PROCESS FOR PREPARING N-(1,1-DIMETHYL-3-OXOBUTYL)ACRYLAMIDE FROM A 2-VINYL-1,3(4H)OXAZINE SULFATE

BACKGROUND OF THE INVENTION

This invention relates to a process for the preparation of diacetone acrylamide, also known as N-(1,1-dimethyl-3- oxobutyl) acrylamide, by the neutralization or alkalization of 5,6-dihydro-6-hydroxy-4,4,6-trimethyl-2-vinyl-1,3(4H)-oxazine sulfate (1:1), which is represented by formula (I), under carefully controlled conditions.

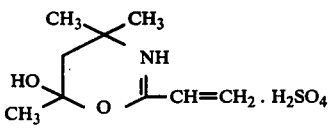

In related U.S. Pat. application, Ser. No. 920,040, filed June 28, 1978, which is incorporated by reference, the preparation of the compound of formula (I) and a new process for the preparation of diacetone acrylamide (DIAC) utilizing the above-mentioned compound as an intermediate is disclosed. Generally, this new process comprises alkalizing or neutralizing a solution of the compound of formula (I) in a water-immiscible organic solvent with an aqueous solution of an alkalizing agent, and recovering the DIAC from the organic solution.

The process of this invention is different from and has advantages over the above related U.S. application process in that it is simpler to carry out, thus increasing the productivity of the process about 60%, and there is less loss of the final product due to dissolution in an aqueous phase, about 5% loss versus about 10-15%.

Applicants are not aware of any prior art reference which, in their judgment as ones skilled in the art of preparing diacetone acrylamide, would anticipate or render obvious the process of the instant invention; however, for the purpose of fully developing the background of the invention and establishing the state of the requisite art, the following additional references are set forth.

In U.S. Pat. No. 3,649,688, an improved method is disclosed for preparing DIAC by reacting acrylonitrile with diacetone alcohol in the presence of sulfuric acid, the improvement comprising preparing a mixture of acrylonitrile and sulfuric acid, said sulfuric acid being at least 93% concentration and the molar ratio of sulfuric acid to acrylonitrile being at least 1.6 to 1, introducing the diacetone alcohol into said mix at a temperature below 30° C. and maintaining said temperature during the reaction of the alcohol with the acrylonitrile, and recovering the DIAC from the reaction mixture. However, the product obtained is yellow-colored and contains about 5-10% by weight of by-product acrylamide.

In U.S. Pat. No. 3,542,867, an improved method is disclosed for preparing diacetone acrylamide by reacting diacetone alcohol, or mesityl oxide, or at least 2 moles of acetone in the presence of acrylonitrile and sulfuric acid, the improvement consisting of diluting the reaction mixture with water to a sulfuric acid content of 25-80% by weight, extracting the DIAC from the acidic reaction mixture with a water-immiscible organic solvent and recovering the DIAC from the extract.

In U.S. Pat. No. 3,542,875, an improved method is disclosed for preparing DIAC by reacting one mole of acrylonitrile with at least one mole of diacetone alcohol or mesityl oxide, or with at least two moles of acetone, in the presence of at least one mole of sulfuric acid, neutralizing the reaction mixture by addition of alkali to a pH at least above 7.5 and subsequently extracting with a water-immiscible organic solvent and recovering DIAC therefrom, the improvement consisting of heating the organic solution of DIAC at 50–100° C. with aqueous alkali and recovering DIAC from the organic solution.

The DIAC produced by the process of the subject invention has advantages over that produced by the processes of references U.S. Pat. Nos. 3,542,867 and 3,542,875 in that it contains less by-product acrylamide as an impurity.

In general, the prior art teaches the preparation of DIAC by reacting acrylonitrile and 4-hydroxy-4-methyl-2-pentanone in the presence of at least 93% sulfuric acid, the mole ratios of said sulfuric acid and acrylonitrile to said 4-hydroxy-4-methyl- 2-pentanone being about 1–2 and 1–1.5 moles, respectively, at a temperature below 15° C., allowing the reaction mixture to warm up to ambient to moderately elevated temperatures to complete the reaction, cooling the reaction mixture, contacting the reaction mixture with water and a water-immiscible organic solvent, neutralizing the aqueous phase with an alkalizing agent, separating the organic phase, stripping the organic phase of volatile materials, and recovering N-(1,1-dimethyl-3-oxobutyl)acrylamide therefrom.

DIAC is useful in photographic films, adhesives, as a reactive cross-linking monomer in unsaturated polyester resins, as a stabilizer in paper and glass reinforced prepregs, and as an additive in hydrocarbon oils. For a description of how to use as an oil additive, see for example, U.S. Pat. No. 3,227,056, Example 18, which is incorporated herein by reference.

In order to obtain DIAC of acceptable color and purity for use in photographic films, it has been generally necessary either to distill or recrystallize the crude product.

There is a need, therefore, for a process that will give high yields of essentially colorless DIAC, having a melting point above 54° C., which does not have to be purified by subsequent recrystallization or distillation.

SUMMARY OF THE INVENTION

In accordance with the present invention, there is provided a process for preparing N-(1,1-dimethyl-3-oxobutyl)acrylamide comprising (1) contacting a dispersion of 5,6-dihydro-6-hydroxy-4,4,6-trimethyl-2-vinyl-1,3(4H)-oxazine sulfate (1:1) with a neutralizing or alkalizing amount of a concentrated aqueous solution of a sodium-containing alkali in a water-immiscible organic solvent to form a hydrated sodium sulfate, while allowing the temperature to rise to about 30° to 35° C., and then cooling the reaction mixture to about 15° to 30° C. to crystallize said hydrated sodium sulfate; (2) separating the crystals of hydrated sodium sulfate; (3) cooling the organic mother liquors recovered from step (2) to about −10° C. to 20° C. to crystallize N-(1,1-dimethyl-3-oxobutyl)acrylamide therefrom; and (4) recovering the crystals of N-(1,1-dimethyl-3-oxobutyl)acrylamide, washing with a cold water-immiscible organic solvent, and drying the same.

In a preferred embodiment, the reaction mixture in step (1) is heated to 35°–50° C. to form a two-phase liquid mixture consisting of an organic phase and molten hydrated sodium sulfate; in step (2), the molten hydrated sodium sulfate is separated; and steps (3) and (4) are as previously described.

In a more preferred embodiment, the additional steps of (a) contacting the organic phase recovered from step (2) with a decolorizing agent, optionally also with a filter aid, and (b) separating said decolorizing agent and optional filter aid from the organic phase are carried out before carrying out steps (3) and (4).

In an especially preferred emobdiment, the mother liquor plus wash liquor recovered in step (4) is diluted with 10-20% by volume of fresh organic solvent and recycled in step (1).

In addition to the advantages previously described, the present invention eliminates the need for azeotropically drying and concentrating the organic solution containing the desired product, and offers better environmental control.

DESCRIPTION OF THE PREFERRED EMBODIMENTS

The process of the present invention may be divided into the following stages:

1. NEUTRALIZATION OR ALKALIZATION OF THE COMPOUND OF FORMULA (I)

The compound of formula (I) is added to a stirred water-immiscible organic solvent in which DIAC is soluble, at ambient temperature, using about 1.5-2.0 mls, preferably about 1.7-1.8 mls, of said water-immiscible organic solvent per gram of the compound of formula (I).

Suitable water-immiscible organic solvents include naphtha, chloroform, methyl isobutyl ketone, dibutyl ether, aromatic hydrocarbons such as benzene, toluene, xylene, and the like. The preferred water-immiscible organic solvent is toluene.

A sufficient amount of a concentrated aqueous solution of a sodium-containing alkali such as sodium hydroxide, sodium carbonate, or sodium bicarbonate is added to the resulting two-phase mixture in an amount sufficient to neutralize the compound of formula (I), or provide a slight excess of alkali.

Preferably, 50% caustic soda is added to the resulting two-phase mixture at about 15° to 50° C., preferably about 30° to 35° C., to neutralize or alkalize the compound of formula (I) and form a two-phase mixture of a solution of DIAC in the water-immiscible organic solvent and insoluble by-product hydrated sodium sulfate. Preferably, the amount of caustic soda added should be about a 1.5% molar excess over that required to neutralize the compound of formula (I). The amount of 50% caustic soda used ranges from about 0.4 to 0.8 gram, preferably about 0.55 to 0.65 gram per gram of the compound of formula (I).

On completion of the addition, the temperature may be between 15° and 50° C., preferably between 30° and 35° C., depending on the method of separating the hydrated sodium sulfate.

2. SEPARATION OF HYDRATED SODIUM SULFATE

After completion of the addition of the sodium-containing alkali in (1), the reaction mixture is optionally cooled to about 10° to 25° C., preferably to about 15° to 20° C., and stirred thereat for about 1-2 hours. The crystals of hydrated sodium sulfate which separate from the solution are isolated by conventional means, such as filtration or centrifuging.

Preferably, on completion of the addition of 50% caustic soda, the reaction mixture is heated to about 33°-50° C., preferably to about 40° to 45° C., to melt the hydrated sodium sulfate and form an insoluble liquid phase. The stirring is then stopped and, after allowing the two liquid phases to settle, the lower phase of molten hydrated sodium sulfate is separated. The DIAC may then be recovered from the residual organic solution as described in sections (3) and (4) which follow.

3. THE CRYSTALLIZATION OF DIAC

The organic mother liquor recovered from (2) is cooled to about −10° C. to 20° C., preferably about −8° C. to 10° C., and held thereat for about ½ - 4 hours, preferably about 1-2 hours, to crystallize the DIAC from the solution.

Preferably, the organic mother liquor recovered from (2) is stirred with about 0.01 to 0.1, preferably about 0.03 to 0.04, part by weight of a decolorizing agent per part by weight of the compound of formula (I) used, at about 30°-45° C., preferably about 30°-35° C., for about ½ - 1 hour to remove colored impurities; the mixture is then clarified before cooling to crystallize DIAC therefrom.

Suitable decolorizing agents include materials such as Super-Filtrol ® (Filtrol Corp.), an acidified clay; Alcoa F-1 (Aluminum Corp. of America), an activated alumina; Darco ® G-60 Decoloring Carbon (Atlas Chemical Industries, Inc.); RB Carbon, and the like. The preferred decolorizing agent is Super-Filtrol ®, used in an amount of about one part by weight per 50 parts by volume of solution treated.

Preferably, about 0.012 part by weight of a filter aid, such as Hyflo Super-Cel ® (Johns-Manville), per part by weight of the compound of formula (I) is added to the organic solution prior to clarification to facilitate the removal of the decolorizing agent.

After clarification, the residual decolorizing agent and filter aid are washed with about 0.05 to 0.1 ml of water-immiscible organic solvent per gram of compound of formula (I) used, preferably toluene, and the washings are added to the clarified solution. The clarified solution plus wash liquor is then cooled, as described previously, to crystallize the DIAC therefrom.

4. THE RECOVERY OF CRYSTALLINE DIAC

The crystalline DIAC is recovered by conventional means, washed with cold water-immiscible solvent, preferably toluene at −8° C., or lower, and dried. The initial yield of DIAC based on the compound of formula (I) is about 55-70% of theoretical.

In an especially preferred embodiment, the mother liquor, plus wash liquor recovered in (4), is diluted with 10-20%, preferably about 15%, by volume of fresh water-immiscible organic solvent, preferably toluene, and recycled in (1). Recycling the mother liquor from (4) to (1) increases the yield of DIAC to about 82-89% of theoretical.

The final product obtained melts above 54° C. and contains less than 0.1% by weight of acrylamide.

The following examples further illustrate the invention. All parts and percentages are by weight unless otherwise specified. All ranges expressed are inclusive of both numbers.

EXAMPLE 1

Preparation of 5,6-Dihydro-6-Hydroxy-4,4,6-Trimethyl-2-Vinyl-1,3(4H)-Oxazine Sulfate (1:1)

Sulfuric acid (392 grams; 98% real; 3.92 moles) is cooled to 0° C. and a mixture of acrylonitrile (113.5 grams; 2.14 moles) and diacetone alcohol (203.5 grams; 1.75 moles) is added thereto over 1.5 hours while maintaining the temperature at 0°–5° C. The resulting mixture is stirred at 0°–5° C. for 0.5 hour, allowed to warm up slowly to 40°–42° C., held thereat for 3 hours and then cooled at 15° C.

Acetone (443 grams; 0.625 ml/gram of reaction mixture) is added to the reaction mixture while keeping the temperature at 15°–20° C. Upon completion of the addition, the solution is cooled to 0°–5° C. and held thereat for 4 hours. The resulting crystals are separated by filtration, washed with acetone and dried to obtain 234 grams of product. The yield of crude product is 50% of theoretical based on diacetone alcohol.

Calculated for $C_9H_{17}NO_6S$: C, 40.45%, H, 6.41%; N, 5.24%; S, 11.97%. Found: C, 39.77%; H, 6.35%; N, 5.10%; S, 11.74%; $H_2O$, 1.55%. Corrected for 1.55% $H_2O$: C, 40.40%; H,6.28%; N,5.18%; S,11.92%. Calculated for $H_2SO_4$: 36.7%. Found: 36.6%.

EXAMPLE 2

The following example illustrates the closest process of the prior art.

A solution of 50% caustic soda (33 mls) in 75 mls of water is slowly added to a stirred slurry of the product of Example 1 (42.5 grams; 0.16 mole) in toluene (100 mls) while maintaining the temperature at 10°–15° C. Upon completion of the addition, the reaction mixture is stirred at 10°–15° C. for an additional 30 minutes and the lower aqueous phase is separated. The toluene layer is then concentrated under vacuum to ⅓ of its original volume and then stored at 6° C. for about 15 hours. The resulting slurry is then filtered and the crystals are dried to obtain 13.74 grams of DIAC, 51% of theoretical based on the product of Example 1.

EXAMPLE 3

The following example illustrates a process of the present invention wherein hydrated sodium sulfate is separated from a toluene solution of DIAC in the liquid state.

The product from Example 1 (170 grams; 0.637 mole) is added to toluene (300 mls) and 50% caustic soda (70 mls) is cautiously added to the mixture while stirring and allowing the temperature to rise to 30°–35° C. When the addition is completed, the reaction mixture is warmed to 40°–45° C., the stirring is stopped and, after allowing the two liquid phases to settle, the bottom layer of molten hydrated sodium sulfate is separated therefrom.

The remaining toluene solution is treated with 6.0 grams of Super-Filtrol ® (Filtrol Corporation, Los Angeles, Calif.) and 2.0 grams of a filter aid, Hyflo Super-Cel ®, (Johns-Manville) at 30°–35° C., and filtered. The filter cake is then washed with toluene (10 mls) and the filtrate plus wash liquor is cooled to 1°–3° C., and held thereat for one hour. The resulting white crystals are recovered by filtration, rinsed with 75 mls of cold (−8° C. to −10° C.) toluene, and dried. The yield of product is 66% of theoretical based on the product of Example 1 charged.

Recycling recovered toluene mother liquors in order reactions carried out in the manner described above increases the overall yield to about 85% of theoretical.

EXAMPLE 4

The following example illustrates a process of the present invention wherein hydrated sodium sulfate is separated from a toluene solution of DIAC in the solid state.

The product of Example 1 (170 grams; 0.637 mole) is stirred with toluene (250 mls) to form a slurry and 50% caustic soda (68 mls) is cautiously added thereto while maintaining the temperature at 30°–35° C. The reaction mixture is then cooled to 15°–20° C. and stirred thereat for 2 hours. The resulting crystalline precipitate of hydrated sodium sulfate is separated by filtration and washed with toluene (50 mls). The combined filtrate and wash liquor are then stirred with Super-Filtrol ® (6 grams) and Hyflo Super-Cel ® (2 grams) at 30° C. for 30 minutes. The insolubles are then separated by filtration and washed with toluene (10 mls). The combined filtrate plus wash liquor is cooled to 5°–10° C. and aged thereat for one hour to crystallize the product. The resulting crystals are recovered by filtration, washed with cold (−10° C.) toluene (50 mls) and dried. The yield of DIAC 59.3 grams, 55% of theoretical based on the product of Example 1 charged. The white crystals melt at 55.2°–57.5° C.

In the manner described above, omitting the Super-Filtrol ® and Hyflo Super-Cel ®, the product obtained is yellowish in color.

EXAMPLE 5

The procedure of Example 4 is followed in every detail except that the initial toluene used to form the slurry is a mixture of 260 mls of mother liquors recovered from the isolation of the product of Example 4 and 40 mls of fresh toluene. There is obtained 77.3 grams of white crystalline DIAC, 71.84% of theoretical, which melts at 55.5°–57.7°·C.

The above example illustrates the greatly increased yield obtained with recycled toluene mother liquor.

EXAMPLE 6

The procedure of Example 5 is followed in every detail except that the toluene used to form the initial slurry is a mixture of the mother liquors recovered from the isolation of the product of Example 5 and sufficient fresh toluene to make a total of 300 mls. The white crystalline DIAC is recovered in two crops; the first crop (90.07 grams) is collected at 8°–10° C., and the second crop (40.9 grams) is collected at 4°–5° C. The overall yield from Example 4 is 82.7% of theoretical.

We claim:

1. A process for preparing N-(1,1-dimethyl-3-oxobutyl)acrylamide comprising (1) contacting a dispersion of 5,6-dihydro-6-hydroxy-4,4,6-trimethyl-2-vinyl-1,3(4H)-oxazine sulfate (1:1) with a neutralizing or alkalizing amount of a concentrated aqueous solution of a sodium-containing alkali in a water-immiscible organic solvent to form a hydrated sodium sulfate, while allowing the temperature to rise to about 30° to 35° C., and then cooling the reaction mixture to about 15° to 30° C. to crystallize said hydrated sodium sulfate; (2) separating the crystals of hydrated sodium sulfate; (3) cooling the organic mother liquors recovered from step (2) to about −10° C. to 20° C. to crystallize N-(1,1-dimethyl-3-oxobutyl)acrylamide therefrom; and (4) recovering the crystals of N-(1,1-dimethyl-3-oxobutyl)acrylamide, washing the recovered crystals with a cold water-immiscible organic solvent, and drying the same.

2. The process of claim 1 which includes the additional steps of (a) contacting the organic mother liquor recovered from step (2) with a decolorizing agent, and (b) separating said decolorizing agent from said organic mother liquor before carrying out steps (3) and (4).

3. The process of claim 1 wherein said sodium-containing alkali is 50% aqueous caustic soda.

4. The process of claim 2 wherein said decolorizing agent is an acidified clay.

5. The process of claim 1 wherein said water-immiscible organic solvent is toluene.

6. The process of claim 1 wherein in step (1) the reaction mixture is heated to 35° to 50° C. to form a two-phase liquid mixture consisting of an organic phase and molten hydrated sodium sulfate, and in step (2) the molten hydrated sodium sulfate is separated before carrying out steps (3) and (4).

7. The process of claim 6 which includes the additional steps of (a) contacting the organic mother liquor recovered from step (2) with a decolorizing agent, and (b) separating said decolorizing agent from said organic mother liquor before carrying out steps (3) and (4).

8. The process of claim 6 wherein said sodium-containing alkali is 50% caustic soda.

9. The process of claim 6 wherein said water-immiscible organic solvent is toluene.

10. The process of claim 7 wherein said decolorizing agent is an acidified clay.

11. The process of claim 1 wherein mother liquor and wash liquor recovered in step (4) are combined, diluted with 15–20% by volume of fresh water-immiscible solvent, and recycled in step (1).

12. The process of claim 6 wherein mother liquor and wash liquor recovered in step (4) are combined, diluted with 15–20% by volume of fresh water-immiscible solvent, and recycled in step (1).

* * * * *